United States Patent
Friedman et al.

(10) Patent No.: US 9,173,864 B2
(45) Date of Patent: Nov. 3, 2015

(54) TREATMENT AND/OR PREVENTION OF INNER EAR CONDITIONS BY MODULATION OF A METABOTROPIC GLUTAMATE RECEPTOR

(75) Inventors: Rick Friedman, Pacific Palisades, CA (US); Benedikt Vollrath, San Diego, CA (US)

(73) Assignee: House Ear Institute, Los Angeles, CA (US)

( * ) Notice: Subject to any disclaimer, the term of this patent is extended or adjusted under 35 U.S.C. 154(b) by 737 days.

(21) Appl. No.: 13/124,883

(22) PCT Filed: Oct. 19, 2009

(86) PCT No.: PCT/US2009/061190
§ 371 (c)(1),
(2), (4) Date: May 27, 2011

(87) PCT Pub. No.: WO2010/048095
PCT Pub. Date: Apr. 29, 2010

(65) Prior Publication Data
US 2011/0263652 A1    Oct. 27, 2011

Related U.S. Application Data

(60) Provisional application No. 61/107,615, filed on Oct. 22, 2008.

(51) Int. Cl.
| | | |
|---|---|---|
| *A61K 31/4192* | (2006.01) | |
| *A61K 31/44* | (2006.01) | |
| *A61K 31/198* | (2006.01) | |
| *A61K 9/00* | (2006.01) | |
| *A61K 9/06* | (2006.01) | |
| *A61K 31/4523* | (2006.01) | |
| *A61K 31/4545* | (2006.01) | |

(52) U.S. Cl.
CPC ............ *A61K 31/198* (2013.01); *A61K 9/0046* (2013.01); *A61K 9/06* (2013.01); *A61K 31/4192* (2013.01); *A61K 31/44* (2013.01); *A61K 31/4523* (2013.01); *A61K 31/4545* (2013.01)

(58) Field of Classification Search
CPC ........................... A61K 31/4192; A61K 31/44
USPC ........................................................ 514/333
See application file for complete search history.

(56) References Cited

U.S. PATENT DOCUMENTS

| | | | |
|---|---|---|---|
| 5,503,848 A | 4/1996 | Perbellini et al. | |
| 6,316,011 B1 | 11/2001 | Ron et al. | |
| 6,392,036 B1 | 5/2002 | Karlsson et al. | |
| 6,740,664 B2 | 5/2004 | Cagle et al. | |
| 7,001,615 B1 | 2/2006 | Singh et al. | |
| 7,425,556 B2 * | 9/2008 | Chapdelaine et al. | ........ 514/248 |
| 7,524,834 B2 | 4/2009 | Karlsson et al. | |
| 8,030,297 B2 | 10/2011 | Lichter et al. | |
| 2004/0082509 A1 | 4/2004 | Bonny | |
| 2004/0101560 A1 | 5/2004 | Sawchuk et al. | |
| 2005/0147585 A1 | 7/2005 | Schwarz | |
| 2005/0214338 A1 | 9/2005 | Guitton et al. | |
| 2006/0013858 A1 | 1/2006 | Trune | |
| 2006/0046970 A1 | 3/2006 | Bowman et al. | |
| 2006/0063802 A1 | 3/2006 | Guitton et al. | |
| 2006/0074083 A1 | 4/2006 | Kalvinsh et al. | |
| 2006/0264897 A1 | 11/2006 | Lobl et al. | |
| 2006/0269602 A1 | 11/2006 | Dasch et al. | |
| 2007/0178051 A1 | 8/2007 | Pruitt et al. | |
| 2007/0299113 A1 | 12/2007 | Kalvinsh et al. | |
| 2008/0103118 A1 | 5/2008 | Clement et al. | |
| 2009/0239919 A1 * | 9/2009 | Wood et al. | .................. 514/371 |
| 2009/0291988 A1 * | 11/2009 | Oballa | ......................... 514/357 |
| 2009/0297533 A1 | 12/2009 | Lichter et al. | |
| 2009/0306225 A1 | 12/2009 | Lichter et al. | |
| 2009/0324552 A1 | 12/2009 | Lichter et al. | |
| 2009/0325938 A1 | 12/2009 | Lichter et al. | |
| 2010/0004225 A1 | 1/2010 | Lichter et al. | |
| 2010/0015228 A1 | 1/2010 | Lichter et al. | |
| 2010/0015263 A1 | 1/2010 | Lichter et al. | |
| 2010/0016218 A1 | 1/2010 | Lichter et al. | |
| 2010/0016450 A1 | 1/2010 | Lichter et al. | |
| 2010/0021416 A1 | 1/2010 | Lichter et al. | |
| 2010/0022661 A1 | 1/2010 | Lichter et al. | |
| 2010/0036000 A1 | 2/2010 | Lichter et al. | |
| 2010/0197800 A1 | 8/2010 | Friedman | |
| 2011/0166060 A1 | 7/2011 | Simons et al. | |

FOREIGN PATENT DOCUMENTS

| | | |
|---|---|---|
| WO | WO 97/38698 | 10/1997 |
| WO | WO 99/24051 | 5/1999 |
| WO | WO 03/034979 | 5/2003 |
| WO | WO 2003/017990 | 6/2003 |

(Continued)

OTHER PUBLICATIONS

Ahn et al., "Lipoic acid rescues DBA mice from early-onset age-related hearing impairment," Neuroreport 19(13):1265-9, 2008.

Arnold et al., "Novel slow- and fast-type drug release round-window microimplants for local drug application to the cochlea: an experimental study in guinea pigs," Audiol Neurootol 10(1):53-63, 2005.

Auris Medical, press release reporting initiating of phase I/II clinical trial with AM-101, Feb. 22, 2007.

Aurts Medical, press release reporting results of phase I/II clinical trial with AM-III, Jun. 21, 2006.

(Continued)

*Primary Examiner* — Sreeni Padmanabhan
*Assistant Examiner* — Sahar Javanmard
(74) *Attorney, Agent, or Firm* — Linda B. Huber; Nixon Peabody LLP

(57) ABSTRACT

Described herein are compositions and methods of treating and/or preventing inner ear conditions by administering to a patient in need thereof a modulator of a metabotropic glutamate receptor.

5 Claims, 1 Drawing Sheet

(56) References Cited

FOREIGN PATENT DOCUMENTS

| WO | WO 03/071986 | 9/2003 |
|---|---|---|
| WO | WO 2007/031098 | 3/2007 |
| WO | WO 2007/031280 | 3/2007 |
| WO | WO 2007/038949 | 4/2007 |
| WO | WO 2007/040982 | 4/2007 |
| WO | WO-2007-045876 A1 | 4/2007 |
| WO | WO 2007/148113 | 12/2007 |
| WO | WO 2008/076556 | 6/2008 |
| WO | WO 2008/155588 | 12/2008 |
| WO | WO-2010-048095 A2 | 4/2010 |
| WO | WO-2010-048095 A3 | 4/2010 |

OTHER PUBLICATIONS

Battaglia et al., "Combination therapy (intratympanic dexamethasone + high-dose prednisone taper) for the treatment of idiopathic sudden sensorineural hearing loss," Otol Neurotol 29(4):453-60, 2008.

Campbell et al., "Oral-D-methionine (MRX-1024) significantly protects against cisplatin-induced hearing loss: a phase II study in humans," Abst $32^{nd}$ Ann MidWinter Res Meeting, ARO Abstracts 32:7, Feb. 14-19, 2009.

Chen and Nathans, "Estrogen-related receptor beta/NR3B2 controls epithelial cell fate and endolymph by the stria vascularis," Dev Cell 13(3):325-37, 2007.

Chen et al., "Design and preparation of thermosensitive in situ gel of dexamethasone sodium phosphate," J Guangdong Coll Pharrn 23(5):518-21, 2007 (English abstract).

Chen et al., "Evaluation of thermosensitive in situ gel using dynamic rheological experiment," Chin Pharm J 43(6):444-447, 2008 (English abstract).

Chen et al., "In vivo distribution and pharmacokinetics of dexamethasone sodium phosphate thermosensitive in situ gel following intratympanic injection," Sichuan Da Xue Xue Bao Yi Xue Ban 37(3):456-9, 2006 (English translation).

Chen et al., "Preparation and characterization of dexamethasone acetate-loaded solid lipid nanoparticles," Chinese J Pharm 39(4):261-264, 2008 (English abstract).

Chen et al., "Study on dexamethasone thermosensitive in situ gel for treating deafness," Chin Pharm J 41(9):685-688, 2006 (English abstract).

Ciprodex, product label, 2009.

Derin et al., "The effects of L-carnitine on presbyacusis in the rat model," Clin Otolaryngol Allied Sci 29(3):238-41, 2004.

Doleviczenyi et al., "Cochlear dopamine release is modulated by group II metobotropic glutamate receptors via GABAergic neurotransmission," Neuroscience Letters 385:93-98 (2005).

Dourmishev et al., "Waardenburg syndrome," Intl J Dermatol 39:656-663 (1999).

Endo et al., "Novel strategy for treatment of inner ears using a biodegradable gel," Laryngoscope 115(11):2016-20, 2005.

Feng et al., Zhonghua er Bi Yan Hou Tou Jing Wai Ke Za Zhi, Jun. 2007;42(6):443-6 (English Abstract).

Feng et al., Zhonghua Yi Xue Za Zhi, Aug. 28, 2007;87(32):2289-91 (English Translation).

Fernandez et al., "Self-curing controlled release systems for steroids. Application of prednisolone-based polymeric systems to ear diseases," Biotnaterials 26(16):3311-8, 2005.

Friedman et al., "GRM7 variants confer susceptibility to age-related hearing impairment," Hum Mol Genet 18(4):785-96, 2009.

Garduno-Anaya et al., "Dexamethasone inner ear perfusion by intratympanic injection in unilateral Ménière's disease: a two-year prospective, placebo-controlled, double-blind, randomized trial," Otolaryngol Head Neck Surg 133(2):285-94, 2005.

Gubbels et al., "Functional auditory hair cells produced in the mammalian cochlea by in utero gene transfer," Nature 455(7212):537-41, 2008.

Guyot et al., "Intratympanic application of an antiviral agent for the treatment of Ménière's disease," ORL J Otorhinolaryngol Relat Spec 70(1):21-6; discussion 26-7, 2008.

Hall et al., "Anti-Pneumocystis Activities of Aromatic Diamidoxine Prodrugs," Antimicrobial Agents & Chemotherapy, 1998, American Society for Microbiology 42(4):666-674 (1998).

Hargunani et al., "Intratympanic injection of dexamethasone: time course of inner ear distribution and conversion to its active form," Otol Neurotol 27(4):564-9, 2006.

Harris et al., "Prevention of noise-induced hearing loss with Src-PTK inhibitors," Hear Res 208(1-2):14-25, 2005.

Harris et al., "Treatment of corticosteroid-responsive autoimmune inner ear disease with methotrexate: a randomized controlled trial," JAMA 290(14):1875-83, 2003.

Hill et al., "Cisplatin-induced ototoxicity: effect of intratympanic dexamethasone injections," Otol Neurotol 29:1005-11, 2008.

Hoffer. et al., "Transtympanic management of tinnitus," Otolaryngol Clin North Am 36(2):353-8, 2003.

Hoshino et al., "The non-steroidal anti-inflammatory drugs protect mouse cochlea against acoustic injury," Tohoku J Exp Med 216(1):53-9, 2008.

Inaoka et al., "Local application of hepatocyte growth factor using gelatin hydrogels attenuates noise-induced hearing loss in guinea pigs," Acta Otolaryngol 129(4):453-7, 2009.

Jia et al., "Intratympanic dexamethasone for refractory sudden deatness," Lin Chung Er Bi Yan Hou Tou Jing Wai Ke Za Zhi 22(7):309-11, 2008 (English translation).

Kazama et al., "Lithium effectively complements vasopressin V2 receptor antagonist in the treatment of hyponatraemia of SIADH rats," Nepbrol Dial Transplant 22(1):68-76,2007.

Keith Ley et al., "GDNF protects the cochlea against noise damage," Neuroreport 9(10):2183-7, 1998.

Kim et al., "Effects of tumor necrosis factor alpha antagonist, platelet activating factor antagonist, and nitric oxide synthase inhibitor on experimental otitis media with effusion," Ann Otol Rhinol Laryngol 115(8):617-23, 2006.

Kitahara et al., "Up-regulation of cochlear aquaporin-3 mRNA expression after intra-endolymphatic sac application of dexamethasone," Neurol Res. 25(8):865-70, 2003.

Lamm and Arnold, "The effect of prednisolone and non-steroidal anti-inflammatory agents on the normal and noise-damaged guinea pig inner ear," Hear Res 115(1-2):149-61, 1998.

Lavreysen and Dautzenberg, "Therapeutic potential of group III metabotropic glutamate receptors," Curr Med Chem 15(7):671-84, 2008.

Lee et al., "Novel therapy for hearing loss: delivery of insulin-like growth factor 1 to the cochlea using gelatin hydrogel," Otol Neurotol 28(7):976-81, 2007.

Lee et al., "Regional delivery of vancomycin using pluronic F-127 to inhibit methicillin resistant *Staphylococcus aureus* (MRSA) growth in chronic otitis media in vitro and in vivo," J Control Release 96(1):1-7, 2004.

Liu et al., "Permeability of different Dexamethasone drugs through round window membrane," Zhonghua Er Bi Yan Hou Tau Jing Wai Ke Za Zhi 41(3):211-5, 2006 (English abstract).

McCarthy et al., "Alport syndrome: a review," Clinical Eye and Vision Care 12:139-150(2000).

McGuinness and Shepherd "Exogenous BDNF rescues rat spiral ganglion neurons in vivo," Otol Neurotol 26(5):1064-72, 2005.

Meltser et al., "Estrogen receptor beta protects against acoustic trauma in mice," J Clin Invest 118(4):1563-70, 2008.

Miceli et al., "Molecular pharmacology and therapeutic potential of neuronal Kv7-modulating drugs," Curr Opin Pharmacol 8(1):65-74, 2008.

Mitsukawa et al., "A selective metabotropic glutamate receptor 7 agonist: activation of receptor signaling via an allosteric site modulates stress parameters in vivo," Proc Natl Acad Sci U S A 102(51):18712-7, 2005.

Nakagawa and Ito, "Local drug delivery to inner ear for treatment of hearing loss," Curr Drug Ther 3:143-147, 2008.

Nance et al., "The Genetics of Deafness," Mental Retardation and Developmental Disabilities, 2003, Wiley-Liss, vol. 9, pp. 109-119.

(56) References Cited

OTHER PUBLICATIONS

Nishimaki et al., "Reduction of metabotropic glutamate receptor-mediated heterosynaptic inhibition of developing MNTB-LSO inhibitory synapses," Eur J Neurosci 26(2):323-30,2007.
Nouvian et al., "Degeneration of sensory outer hair cells following pharmacological blockade of cochlear KCNQ channels in the adult guinea pig," Eur J Neurosci 17(12):2553-62, 2003.
Park et al., "Effect of inhibitor of tumor necrosis factor-alpha and oxatomide on immune mediated otitis media," Laryngoscope 116(9):1642-6, 2006.
Parnes et al., "Corticosteroid pharmacokinetics in the inner ear fluids: an animal study followed by clinical application," Laryngoscope 109(7 Pt 2 Supplement No. 91):1-17, 1999.
Paulson et al., "A novel controlled local drug delivery system for inner ear disease," Laryngoscope 118(4):706-11, 2008.
Peng et al., "Clinical investigation of different routes of administration of dexamethasone on sudden deafness," Lin Chung Er Bi Yan Hou Tou Jing Wai Ke Za Zhi 22(10):442-5, 2008 (English translation).
Peng et al., "Group I metabotropic glutamate receptors in spiral Ganglion neutrons contribute to excitatory neurotransmissions in the cochlea," Neuroscience 123:221-230 (2004).
Plontke et al., "Rapid clearance of methylprednisolone after intratympanic application in humans. Comment on: Bird PA, Begg EJ, Zhang M, et al. Intratympanic versus intravenous delivery of methylprednisolone to cochlear perilymph. Otol Neurotol 2007; 28:1124-30," Otol Neurotol 29(5):732-3, 2008.
Pondugula et al., "Glucocorticoid regulation of genes in the amiloride-sensitive sodium transport pathway by semicircular canal duct epithelium of neonatal rat," Physiol Genomics 24(2):114-23, 2006.
Pondugula et al., "Glucocorticoids stimulate cation absorption by semicircular canal duct epithelium via epithelial sodium channel," Am J Physiol Renal Physiol 286(6):F1127-35, 2004.
Psillas et al., "Potential efficacy of early treatment of acute acoustic trauma with steroids and piracetam after gunshot noise," Eur Arch Otorhinolaryngol 265(12):1465-9, 2008.
Puel, "Chemical synaptic transmission in the cochlea," Prog Neurobiol 47(6):449-76, 1995.
Salt at al., "Local Inner Ear Drug Delivery and Pharmacokinetics," Drug Discovery Today 10(19):1299-1306 (2005).
Satoh et al., "Tumor necrosis factor-alpha, an initiator, and etanercept, an inhibitor of cochlear inflammation," Laryngoscope 112(9):1627-34, 2002.
Schoepp et al., "Pharmacological agents acting at subtypes of metabotropic glutamate receptors," Neuropharmacology 38(10):1431-76, 1999.
Seidman et al., "Anti-intercellular adhesion molecule-1 antibody's effect on noise damage," Laryngoscope 119(4):707-12, 2009.
She et al., "A short term study on the efficacies of intratympanic prednisolone and dexamethasone injection for subjective tinnitus," Lin Chung Er Bi Yan Hou Tou Jing Wai Ke Za Zhi 22(19):871-3, 2008 (English translation).
Shepherd et al., "Neurotrophins and electrical stimulation for protection and repair of spiral ganglion neurons following sensorineural hearing loss," Hear Res 242(1-2):100-9, 2008.
Shinohara et al., "Neurotrophic factor intervention restores auditory function in deafened animals," Proc Natl Acad Sci U S A 99(3):1657-60, 2002.
Sun et al., "In vitro permeability or round window membrane to transforming dexamethasone with delivery vehicles—a dosage estimation," Chin Med J (Engl) 120(24):2284-9, 2007.
Suzuki et al., "Pharmacological Characterization of a New, orally Active and Potent Allosteric Metabotropic Glutamate receptor 1 Antagonist, 4-[1-2 {Fluorophyridin-3-yl)-5-methyl-1H-1,2,3-triazol-4-yl]-N-isopropyl-N-methyl-3,6-dihydropyricine-1(2H)-carboxamide (FTIDC)," J Pharmacol Exp Ther 321(3):1144-1153 (2007).
Synphora AB, website printout for JB004/A, 2009.
Tabuchi et al. "Hearing impairment in TRPV4 knockout mice," Neurosci Lett 382(3):304-8, 2005.
Taguchi et al., "Expressions of aquaporin-2, vasopressin type 2 receptor, transient receptor potential channel vanilloid (TRPV)1, and TRPV4 in the human endolymphatic sac," Larynuoscope 117(4):695-8, 2007.
Tahera et al., "NF-kB mediated glucocorticoid response in the inner ear after acoustic trauma," J Neurosci Res 1;83(6):1066-76, 2006.
Takeda and Taguchi, "Aquaporins as potential drug targets for Meniere's disease and its related diseases," Handb Exp Pharmacol 190:171-84, 2009.
Takeda et al., "Decompression effects of erythritol on endolymphatic hydrops," Auris Nasus Larynx 36(2):146-51, 2009.
Takeda et al., "The effects of V2 antagonist (OPC-31260) on endolymphatic hydrops," Hear Res 182(1-2):9-18, 2003.
Takemura et al., "Direct inner ear infusion of dexamethasone attenuates noise-induced trauma in guinea pig," Hear Res 196(1-2):58-68, 2004.
Takumida and Anniko, "Nitric oxide in the inner ear,"Cur Opin Neural 15(1):11-5, 2002.
Tang et al., "COUP-TF1 contols Notch regulation of hair cell and support cell differation," Development 133(18):3683-93, 2006.
The Royal National Institute for Deaf People (RNID), advertisement insert in Nature Reviews Drug Discovery, May 2009.
Thorne et al., "Potential role of purinergic signalling in cochlear pathology," Audiol Neurootol 7(3):180-4, 2002.
Van Wijk et al., "Local perfusion of the tumor necrosis factor alpha blocker infliximab to the inner ear improves autoimmune neurosensory hearing loss," Audiol Neurootol 11(6):357-65, 2006.
Wang et al., "A novel dual inhibitor of calpains and lipid peroxidation (BN82270) rescues the cochlea from sound trauma," Neuropharmacology 52(6): 1426-37, 2007.
Wang et al., "Over-expression of X-linked inhibitor of apoptosis protein slows presbycusis in C57BL/6J mice," Neurobiol Aging Aug. 26, 2008 [Epub ahead of print].
Watanabe et al., "Inhibition of inducible nitric oxide synthase lowers the cochlear damage by lipopolysaccharide in guinea pigs," Free Radic Res 32(4):363-70, 2000.
Watanabe et al., "Nitric oxide synthase inhibitor reduces the apoptotic change in the cisplatin-treated cochlea of guinea pigs," Anticancer Drugs 11(9):731-5, 2000.
Watanabe et al., "Nitric oxide synthase inhibitor suppresses the ototoxic side effect of cisplatin in guinea pigs," Anticancer Drugs 11(5):401-6, 2000.
Yamamoto et al., "Inhibition of Notch/RBP-J signaling induces hair cell formation in neonate mouse cochleas," J Mol Med 84(1):37-45, 2006.
Yang et al., "Intratympanic immunosuppressives for prevention of immune-mediated sensorineural hearing loss," Am J Otol 21(4):499-504, 2000.
Yildirim et al., "Effect of intratympanic dexamethasone on noise-induced temporary threshold shift," Laryngoscope 115(7):1219-22, 2005.
Zheng et al., "Vanilloid receptors in hearing: altered cochlear sensitivity by vanilloids and expression of TRPV1 in the organ of corti," J Neurophysiol 90(1):444-55, 2003.
Zhou et al., "Intratympanic administration of methylprednisolone reduces impact of experimental intensive impulse noise trauma on hearing," Acta Oto-Laryngologica 129:602-607, 2009.
Combined search and examination report in UK Patent Application No. GB0823378.5 dated Feb. 27, 2009.
Combined search and examination report in UK Patent Application No. GB0912650.9 dated Oct. 23, 2009.
Combined search and examination report in UK Patent Application No. GB0907065.7 dated Nov. 16, 2009.
Examination report in UK Patent Application No. GB0823378.5 dated Oct. 23, 2009.
PCT/US2008/061330 International Search Report mailed Jul. 31, 2008.
PCT/US09/61190 Search Report mailed May 14, 2010.
U.S. Appl. No. 12/466,310 Office Action dated Jan. 12, 2011.
U.S. Appl. No. 12/506,091 Office Action dated Feb. 22, 2012.
U.S. Appl. No. 12/504,553 Office Action dated Feb. 14, 2012.
AU 2009307825 Examiner's Report dated Apr. 24, 2012.
EP09822509.7 Search Report dated Mar. 15, 2012.

* cited by examiner

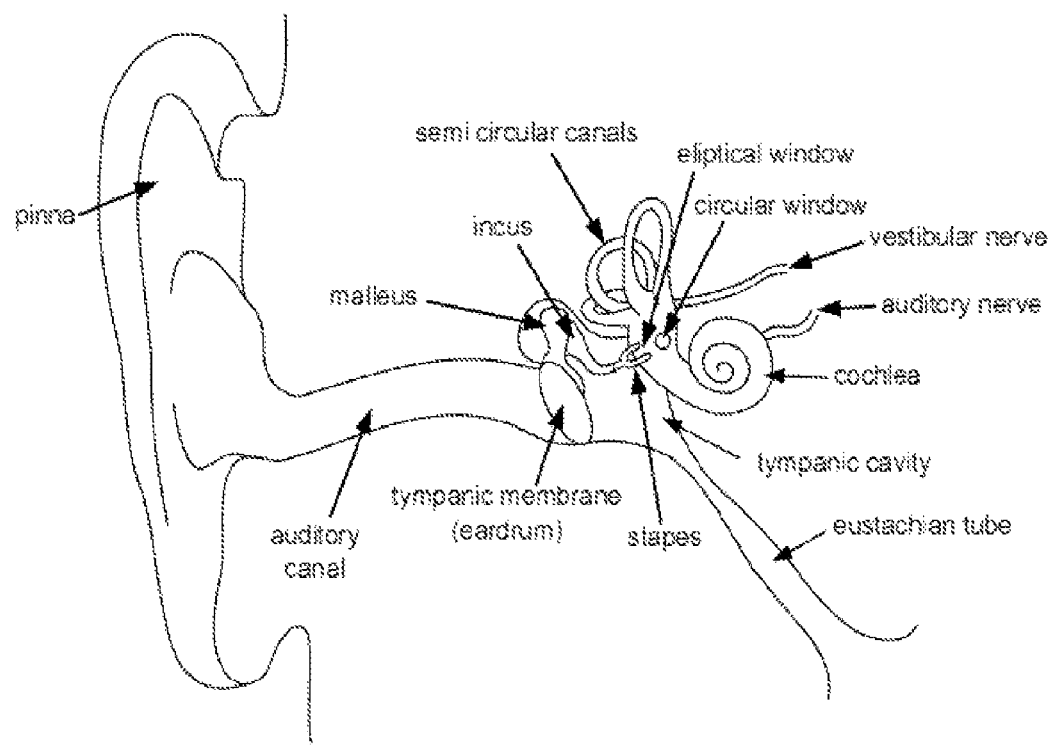

TREATMENT AND/OR PREVENTION OF INNER EAR CONDITIONS BY MODULATION OF A METABOTROPIC GLUTAMATE RECEPTOR

CROSS-REFERENCE

This application is a National Phase Application, under 35 U.S.C. §371, of International Application No. PCT/US2009/061190, filed Oct. 19, 2009, which claims the benefit of U.S. Provisional Application No. 61/107,615, filed Oct. 22, 2008, which application is incorporated herein by reference.

FIELD OF THE INVENTION

Described herein are composition and methods of treatment and/or prevention of inner ear conditions by administering to a patient in need thereof a modulator of a metabotropic glutamate receptor.

BACKGROUND OF THE INVENTION

There are several conditions of the inner ear including noise-induced hearing loss, age-induced hearing loss (e.g. presbycusis), tinnitus and others. Presbycusis is the loss of hearing that gradually occurs in most individuals as they grow older. About 30-35 percent of adults between the ages of 65 and 75 years have a hearing loss. It is estimated that 40-50 percent of people 75 and older have a hearing loss.

The loss associated with presbycusis is usually greater for high-pitched sounds. For example, it may be difficult for someone to hear the nearby chirping of a bird or the ringing of a telephone. However, the same person may be able to hear clearly the low-pitched sound of a truck rumbling down the street.

There are many causes of presbycusis. Most commonly it arises from changes in the inner ear of a person as he or she ages, but presbycusis can also result from changes in the middle ear or from complex changes along the nerve pathways leading to the brain. Presbycusis most often occurs in both ears, affecting them equally. Because the process of loss is gradual, people who have presbycusis may not realize that their hearing is diminishing.

With presbycusis, sounds often seem less clear and lower in volume. This contributes to difficulty hearing and understanding speech. Individuals with presbycusis may experience several of the following: The speech of others seems mumbled or slurred. High-pitched sounds such as "s" and "th" are difficult to hear and tell apart. Conversations are difficult to understand, especially when there is background noise. A man's voice is easier to hear than the higher pitches of a woman's voice. Certain sounds seem annoying or overly loud. Tinnitus (a ringing, roaring, or hissing sound in one or both ears) may also occur.

Currently, treatment options for presbycusis include treatment of postulated underlying causes, such as hypertension; hearing aids or a cochlear implant; assistive listening devices, such as telephone amplifiers; and removal of earwax. There are no clinically proven remedies for hearing loss.

SUMMARY OF THE INVENTION

Described herein are compositions and methods for preventing and/or treating inner ear conditions associated with or characterized by aberrant glutamatergic signaling in the inner ear. The aberrant glutamatergic signaling is prevented or treated by use of modulators of a metabotropic glutamate receptor, including an antagonist, partial agonist, inverse agonist, neutral or competitive antagonist, allosteric antagonist, and/or orthosteric antagonist. In certain embodiments, the inner ear conditions are characterized by excessive glutamate release and/or excitotoxicity. Compositions and methods for such conditions include antagonists (or uses thereof) for a metabotropic glutamate receptor. In certain embodiments, the inner ear conditions are characterized by insufficient glutamate release. Compositions and methods for such conditions include agonists (or uses thereof) for a metabotropic glutamate receptor.

Examples of conditions associated with or characterized by excessive glutamate release and/or excitotoxicity are presbycusis, tinnitus, and noise-induced hearing loss. In certain embodiments, compositions for use in treating such conditions include at least one modulator of a metabotropic glutamate receptor, and the methods include administering to a human a therapeutically effective amount of a pharmaceutical composition comprising a modulator of a metabotropic glutamate receptor. In one embodiment, the modulator is specific to Group I mGluR (such as mGluR1 and/or mGluR5). In a further embodiment, the modulator is selected from an antagonist of Group I mGluR (such as mGluR1 and/or mGluR5).

In certain embodiments, compositions for use in treating conditions associated with insufficient glutamate release include at least one modulator of a metabotropic glutamate receptor, and the methods include administering to a human a therapeutically effective amount of a pharmaceutical composition comprising a modulator of a metabotropic glutamate receptor. In one embodiment, the modulator is specific to Group I mGluR (such as mGluR1 and/or mGluR5). In a further embodiment, the modulator is selected from an agonist of Group I mGluR (such as mGluR1 and/or mGluR5).

In one embodiment, a method of formulating a pharmaceutical composition comprising a modulator of Group I mGluR for treatment and/or prevention of inner ear conditions associated with or characterized by aberrant glutamatergic signaling in the inner ear, such as age-related hearing loss (presbycusis) or noise-induced hearing loss is disclosed. The modulator is an antagonist, partial agonist, inverse agonist, neutral or competitive antagonist, allosteric antagonist, and/or orthosteric antagonist of Group I mGluR. In some embodiments, the pharmaceutical composition is optionally formulated for topical, oral or pump delivery, or via round or oval window delivery.

In another embodiment are pharmaceutical compositions for treating or preventing inner ear conditions associated with or characterized by aberrant glutamatergic signaling in the inner ear: such compositions include immediate release compositions, sustained or controlled release compositions, and combinations thereof. Further, such compositions provide a therapeutic dose of the Group I mGluR modulator to the inner ear of a patient in need, including the cochlea portion of the inner ear. Further, such compositions are optionally administered in the ear, including administration on or near the round window membrane of the inner ear. Such compositions comprise a modulator of a Group I mGluR, such as a selective agonist or antagonist of Group I mGluR.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 illustrates the anatomy of the ear.

DETAILED DESCRIPTION OF THE INVENTION

There is an important and unmet need to develop safer and more effective pharmacologic therapies for treating and/or preventing conditions of the inner ear associated with excessive glutamate release and/or excitotoxicity, including noise-induced hearing loss, age-induced hearing loss (e.g. presbycusis), tinnitus and others. In addition, there is an important and unmet need to develop safer and more effective pharmacologic therapies for treating and/or preventing conditions of the inner ear associated with insufficient glutamate release.

Anatomy of the Ear

As shown in FIG. 1, the outer ear is the external portion of the organ and is composed of the pinna (auricle), the auditory canal (external auditory meatus) and the outward facing portion of the tympanic membrane, also known as the ear drum. The pinna, which is the fleshy part of the external ear that is visible on the side of the head, collects sound waves and directs them toward the auditory canal. Thus, the function of the outer ear, in part, is to collect and direct sound waves towards the tympanic membrane and the middle ear.

The middle ear is an air-filled cavity, called the tympanic cavity, behind the tympanic membrane. The tympanic membrane, also known as the ear drum, is a thin membrane that separates the external ear from the middle ear. The middle ear lies within the temporal bone, and includes within this space the three ear bones (auditory ossicles): the malleus, the incus and the stapes. The auditory ossicles are linked together via tiny ligaments that form a bridge across the space of the tympanic cavity. The malleus, which is attached to the tympanic membrane at one end, is linked to the incus at its anterior end, which in turn is linked to the stapes. The stapes is attached to the oval window, one of two windows located within the tympanic cavity. A fibrous tissue layer, known as the annular ligament connects the stapes to the oval window. Sound waves from the outer ear first cause the tympanic membrane to vibrate. The vibration is transmitted across to the cochlea through the auditory ossicles and oval window, which transfers the motion to the fluids in the auris interna. Thus, the auditory ossicles are arranged to provide a mechanical linkage between the tympanic membrane and the oval window of the fluid-filled auris interna, where sound is transformed and transduced to the auris interna for further processing. Stiffness, rigidity or loss of movement of the auditory ossicles, tympanic membrane or oval window leads to hearing loss, e.g. otosclerosis, or rigidity of the stapes bone.

The tympanic cavity also connects to the throat via the eustachian tube. The eustachian tube provides the ability to equalize the pressure between the outside air and the middle ear cavity. The round window, a component of the auris interna but which is also accessible within the tympanic cavity, opens into the cochlea of the auris interna. The round window is covered by a membrane, which consists of three layers: an external or mucous layer, an intermediate or fibrous layer, and an internal membrane, which communicates directly with the cochlear fluid. The round window, therefore, has direct communication with the auris interna via the internal membrane.

The round window membrane consists of three layers: an outer epithelial layer facing the middle ear, a core of connective tissue and an inner epithelial layer lining the inner ear. Tight junctions are present near the surface of the outer epithelial layer. The core connective tissue is interspersed with blood and lymph vessels. The inner epithelium contains large extracellular spaces that contain amorphous material. Animal studies have shown that the round window membrane behaves like a semipermeable membrane with absorptive capabilities.

Movements in the oval and round window are interconnected, i.e. as the stapes bone transmits movement from the tympanic membrane to the oval window to move inward against the auris interna fluid, the round window is correspondingly pushed out and away from the cochlear fluid. This movement of the round window allows movement of fluid within the cochlea, which leads in turn to movement of the cochlear inner hair cells, allowing hearing signals to be transduced. Stiffness and rigidity in the round window leads to hearing loss because of the lack of ability of movement in the cochlear fluid. Recent studies have focused on implanting mechanical transducers onto the round window, which bypasses the normal conductive pathway through the oval window and provides amplified input into the cochlear chamber.

Auditory signal transduction takes place in the auris interna. The fluid-filled auris interna, or inner ear, consists of two major components: the cochlear and the vestibular apparatus. The auris interna is located in part within the osseous or bony labyrinth, an intricate series of passages in the temporal bone of the skull. The vestibular apparatus is the organ of balance and consists of the three semi-circular canals and the vestibule. The three semi-circular canals are arranged relative to each other such that movement of the head along the three orthogonal planes in space can be detected by the movement of the fluid and subsequent signal processing by the sensory organs of the semi-circular canals, called the crista ampullaris. The crista ampullaris contains hair cells and supporting cells, and is covered by a dome-shaped gelatinous mass called the cupula. The hairs of the hair cells are embedded in the cupula. The semi-circular canals detect dynamic equilibrium, the equilibrium of rotational or angular movements.

When the head turns rapidly, the semicircular canals move with the head, but endolymph fluid located in the membranous semi-circular canals tends to remain stationary. The endolymph fluid pushes against the cupula, which tilts to one side. As the cupula tilts, it bends some of the hairs on the hair cells of the crista ampullaris, which triggers a sensory impulse. Because each semicircular canal is located in a different plane, the corresponding crista ampullaris of each semi-circular canal responds differently to the same movement of the head. This creates a mosaic of impulses that are transmitted to the central nervous system on the vestibular branch of the vestibulocochlear nerve. The central nervous system interprets this information and initiates the appropriate responses to maintain balance. Of importance in the central nervous system is the cerebellum, which mediates the sense of balance and equilibrium.

The vestibule is the central portion of the auris interna and contains mechanoreceptors bearing hair cells that ascertain static equilibrium, or the position of the head relative to gravity. Static equilibrium plays a role when the head is motionless or moving in a straight line. The membranous labyrinth in the vestibule is divided into two sac-like structures, the utricle and the saccule. Each structure in turn contains a small structure called a macula, which is responsible for maintenance of static equilibrium. The macula consists of sensory hair cells, which are embedded in a gelatinous mass (similar to the cupula) that covers the macula. Grains of calcium carbonate, called otoliths, are embedded on the surface of the gelatinous layer.

When the head is in an upright position, the hairs are straight along the macula. When the head tilts, the gelatinous mass and otoliths tilts correspondingly, bending some of the hairs on the hair cells of the macula. This bending action initiates a signal impulse to the central nervous system, which travels via the vestibular branch of the vestibulocochlear nerve, which in turn relays motor impulses to the appropriate muscles to maintain balance.

The cochlea is the portion of the auris interna related to hearing. The cochlea is a tapered tube-like structure which is coiled into a shape resembling a snail. The inside of the cochlea is divided into three regions, which is further defined by the position of the vestibular membrane and the basilar membrane. The portion above the vestibular membrane is the scala vestibuli, which extends from the oval window to the apex of the cochlea and contains perilymph fluid, an aqueous liquid low in potassium and high in sodium content. The basilar membrane defines the scala tympani region, which extends from the apex of the cochlea to the round window and also contains perilymph. The basilar membrane contains thousands of stiff fibers, which gradually increase in length from the round window to the apex of the cochlea. The fibers of the basement membrane vibrate when activated by sound. In between the scala vestibuli and the scala tympani is the cochlear duct, which ends as a closed sac at the apex of the cochlea. The cochlear duct contains endolymph fluid, which is similar to cerebrospinal fluid and is high in potassium.

The organ of Corti, the sensory organ for hearing, is located on the basilar membrane and extends upward into the cochlear duct. The organ of Corti contains hair cells, which have hairlike projections that extend from their free surface, and contacts a gelatinous surface called the tectorial membrane. Although hair cells have no axons, they are surrounded by sensory nerve fibers that form the cochlear branch of the vestibulocochlear nerve (cranial nerve VIII).

As discussed, the oval window, also known as the elliptical window communicates with the stapes to relay sound waves that vibrate from the tympanic membrane. Vibrations transferred to the oval window increases pressure inside the fluid-filled cochlea via the perilymph and scala vestibuli/scala tympani, which in turn causes the membrane on the round window to expand in response. The concerted inward pressing of the oval window/outward expansion of the round window allows for the movement of fluid within the cochlea without a change of intra-cochlear pressure. However, as vibrations travel through the perilymph in the scala vestibuli, they create corresponding oscillations in the vestibular membrane. These corresponding oscillations travel through the endolymph of the cochlear duct, and transfer to the basilar membrane. When the basilar membrane oscillates, or moves up and down, the organ of Corti moves along with it. The hair cell receptors in the Organ of Corti then move against the tectorial membrane, causing a mechanical deformation in the tectorial membrane. This mechanical deformation initiates the nerve impulse which travels via the vestibulocochlear nerve to the central nervous system, mechanically transmitting the sound wave received into signals that are subsequently processed by the central nervous system.

Excitotoxicity

Excitotoxicity refers to the death of or damaging of neurons and/or otic hair cells by glutamate and/or similar substances.

Glutamate is the most abundant excitatory neurotransmitter in the central nervous system. Pre-synaptic neurons release glutamate upon stimulation. It flows across the synapse, binds to receptors located on post-synaptic neurons, and activates these neurons. The glutamate receptors include the NMDA, AMPA, and kainate receptors. Glutamate transporters are tasked with removing extracellular glutamate from the synapse. Certain events (e.g. ischemia or stroke) can damage the transporters. This results in excess glutamate accumulating in the synapse. Excess glutamate in synapses results in the over-activation of the glutamate receptors.

The AMPA receptor is activated by the binding of both glutamate and AMPA. Activation of certain isoforms of the AMPA receptor results in the opening of ion channels located in the plasma membrane of the neuron. When the channels open, Na and $Ca^{2+}$ ions flow into the neuron and $K^+$ ions flow out of the neuron.

The NMDA receptor is activated by the binding of both glutamate and NMDA. Activation of the NMDA receptor, results in the opening of ion channels located in the plasma membrane of the neuron. However, these channels are blocked by $Mg^{2+}$ ions. Activation of the AMPA receptor results in the expulsion of Mg2+ ions from the ion channels into the synapse. When the ion channels open, and the $Mg^{2+}$ ions evacuate the ion channels, Na and $Ca^{2+}$ ions flow into the neuron, and $K^+$ ions flow out of the neuron.

Excitotoxicity occurs when the NMDA receptor and AMPA receptors are over-activated by the binding of excessive amounts of ligands, for example, abnormal amounts of glutamate. The over-activation of these receptors causes excessive opening of the ion channels under their control. This allows abnormally high levels of $Ca^{2+}$ and $Na^+$ to enter the neuron. The influx of these levels of $Ca^{2+}$ and $Na^+$ into the neuron causes the neuron to fire more often. This increased firing yields a rapid buildup of free radicals and inflammatory compounds. The free radicals damage the mitochondria, depleting the cell's energy stores. Further, excess levels of $Ca^{2+}$ and $Na^+$ ions activate excess levels of enzymes including, but not limited to, phospholipases, endonucleases, and proteases. The over-activation of these enzymes results in damage to the cytoskeleton, plasma membrane, mitochondria, and DNA of the neuron. Such damage often results in the activation of apoptotic genes. Additionally, the transcription of multiple pro-apoptotic genes and anti-apoptotic genes are controlled by $Ca^{2+}$ levels. Excess $Ca^{2+}$ often results in the upregulation of the pro-apoptotic genes and the down-regulation of anti-apoptotic genes.

Tinnitus

Tinnitus is the perception of sound in the absence of any external stimuli. It may occur in one or both ears, continuously or sporadically, and is most often described as a ringing sound. It is most often used as a diagnostic symptom for other diseases. There are two types of tinnitus: objective and subjective. The former is a sound created in the body which is audible to anyone. The latter is audible only to the affected individual. Studies estimate that over 50 million Americans experience some form of tinnitus. Of those 50 million, about 12 million experience severe tinnitus. In certain instances, tinnitus results from excitotoxicity caused by abnormal activity of an NMDA receptor.

Presbycusis

There are four different types of presbycusis: Sensory presbycusis results in abrupt loss of the ability to hear high frequencies and tones. Neural presbycusis reduces the ability to understand speech. Strial or metabolic presbycusis produces relatively flat hearing loss. Cochlear conductive presbycusis is characterized by a more gradual loss of the ability to hear high frequencies.

Causes of Presbycusis

Sensorineural hearing loss is caused by disorders of the inner ear or auditory nerve. Presbycusis is usually a sensorineural hearing disorder. It is most commonly caused by gradual changes in the inner ear. The cumulative effects of repeated exposure to daily traffic sounds or construction work, noisy offices, equipment that produces noise, and loud music can cause sensorineural hearing loss. Sensorineural hearing loss is most often due to a loss of hair cells (sensory receptors in the inner ear). This can occur as a result of hereditary factors as well as aging, various health conditions, and side effects of some medicines (aspirin and certain antibiotics).

Presbycusis may be caused by changes in the blood supply to the ear because of heart disease, high blood pressure, vascular (pertaining to blood vessels) conditions caused by diabetes, or other circulatory problems. The loss may be mild, moderate, or severe.

Sometimes presbycusis is a conductive hearing disorder, meaning the loss of sound sensitivity is caused by abnormalities of the outer ear and/or middle ear. Such abnormalities may include reduced function of the tympanic membrane (the eardrum) or reduced function of the three tiny bones in the middle ear that carry sound waves from the tympanic membrane to the inner ear.

Glutamate and Glutamate Receptors

L-glutamate [L-Glu] is the primary excitory amino acid neurotransmitter in the mammalian central nervous system. It activates both ionotropic glutamate receptors (iGluRs) and metabotropic glutamate receptors (mGluRs). The former are coupled to ion-channels and typically mediate fast excitory neurotransmission.

In contrast to the iGluRs, the mGluRs are G-protein coupled receptors functioning via second messenger pathways to modulate neuronal excitability and synaptic efficacy. To date, eight subtypes of mGluRs have been identified, and they can be classified into three groups based on their sequence similarities, second messenger coupling and pharmacology. Group I (mGluR1 and mGluR5) couple to Gq, activate phospholipase C and are selectively activated by 3,5-dihydroxyphenyl glycine (DHPG) at low µM concentration. In contrast, Group II (mGluR2 and mGluR3) and Group III (mGluR4, 6, 7, 8) negatively couple via Gi/Go to adenylate cyclase and inhibit stimulated cAMP formation. Group II mGluRs can be selectively activated by (2S,1'S,2'S)-2-(dicarboxycyclopropyl)glycine (DCG-IV), whereas Group III mGluRs are selectively activated by synthetic agonist L-amino-4-phosphonobutyric acid (L-AP4) and endogenous ligand L-serine-O-phosphate (L-SOP).

Prevention or Treatment of Inner Ear Conditions

Glutamate is also the key neurotransmitter in the auditory system, transducing the signal from the sensory inner hair cells (IHCs) to the afferent auditory nerve fibers. Several diseases of the inner ear, including noise-induced hearing loss, age-induced hearing loss and tinnitus, have been linked to an excessive glutamate release in the IHC-auditory nerve cleft and neuronal damage by excitotoxicity. Therefore, modulators of glutamatergic neurotransmission are useful for directly modulating auditory function in the cochlea and are treatment modalities for inner ear diseases linked to excessive glutamate release. Pre-synaptic neurons release glutamate upon stimulation. It flows across the synapse, binds to receptors located on post-synaptic neurons, and activates these neurons. The glutamate receptors include the NMDA, AMPA, and kainate receptors.

Glutamatergic neurotransmission in the cochlea are modulated by agonists or antagonists to either ionotropic (NMDA and AMPA) or metabotropic glutamate receptors (mGluRs). Thus, as described herein, modulators of Group I mGluRs (such as mGluR1 and mGluR5) are useful for the treatment and/or prevention of inner ear diseases. Modulators of Group I mGluRs disclosed herein are either selective for one Group I mGluR isoform or affect both mGluR1 and mGluR5 with equal or similar efficacy. In both the CNS and the cochlea, Group I mGluRs are generally regarded as postsynaptic receptors, modulating the response of the postsynaptic terminal to glutamate by affecting NMDA- and AMPA-mediated responses. Agonists to Group I mGluRs increase NMDA- and AMPA-mediated responses in the CNS while antagonists reduce these responses. Therefore, antagonists to Group I mGluRs are beneficial in circumstances of excessive glutamate neurotransmission and are treatment modalities for inner ear diseases associated with excessive glutamate release and excitotoxicity.

In some embodiments, the mGluR Group I agonist is ACPD ((1S,3R)-1-aminocyclopentane-1,3-dicarboxylic acid); tADA (trans-Azetidine-2,4-dicarboxylic acid); CHPG ((RS)-2-Chloro-5-hydroxyphenylglycine); (RS)-3-Hydroxyphenylglycine; (S)-3-Hydroxyphenylglycine; RS-3,5-DHPG ((RS)-3,5-Dihydroxyphenylglycine); S-3,5-DHPG ((S)-3,5-Dihydroxyphenylglycine); (±)-trans-ACPD ((±)-1-Aminocyclopentane-trans-1,3-dicarboxylic acid); L-CCG ((2S,1'S,2'S)-2-(carboxycyclopropyl)glycine); L-3'-F2CCG-I ((2S,1'S,2'S)-2-(2'-Carboxy-3',3'-difluorocyclopropyl)glycine); L-Glutamic Acid; MNI-caged-L-glutamate ((S)-a-Amino-2,3-dihydro-4-methoxy-7-nitro-d-oxo-1H-indole-1-pentanoic acid); L-Quisqualic acid; S-Sulfo-L-cysteine sodium salt; CHPG ((RS)-2-chloro-5-hydroxyphenylglycine); UPF 596 ((S)-(+)-2-(3'-Carboxybicyclo[1.1.1] pentyl)-glycine); L-Cysteinesulfinic acid; or combinations thereof.

In some embodiments, the mGluR Group I antagonist is AIDA (1-aminoindan-1,5-dicarboxylic acid); ACDPP (3-Amino-6-chloro-5-dimethylamino-N-2-pyridinylpyrazinec arboxamide hydrochloride; DL-AP3 (DL-2-Amino-3-phosphonopropionic acid); BAY-36-7620 ((3aS,6aS)-Hexahydro-5-methylene-6a-(2-naphthalenylmethyl)-1H-cyclopenta[c]furan-1-one); Fenobam; 4 CPG ((S)-4-carboxyphenylglycine); (S)-4C3HPG ((S)-4-carboxy-3-hydroxyphenylglycine); CPCCOEt (7-hydroxyiminocyclopropan[b]chromen-1a-carboxylic acid ethyl ester); LY 367385 ((S)-(+)-a-Amino-4-carboxy-2-methylbenzeneacetic acid); LY 456236 hydrochloride (6-methoxy-N-(4-methoxyphenyl) quinazolin-4-amine, MPMQ hydrochloride); 3-MATIDA (a-Amino-5-carboxy-3-methyl-2-thiopheneacetic acid); MCPG (a-methyl-4-carboxyphenylglycine); MPEP (2-methyl-6-(phenylethynyl)-pyridine); (MTEP) 3-[(2-methyl-1,3-thiazol-4-yl)ethynyl]-pyridine; PHCCC(N-Phenyl-7-(hydroxyimino)cyclopropa[b]chromen-1a-carboxamide; SIB 1757 (6-Methyl-2-(phenylazo)-3-pyridinol; SIB 1893 (2-Methyl-6-(2-phenylethenyl)pyridine; YM 298198 hydrochloride (6-Amino-N-cyclohexyl-N,3-dimethylthiazolo[3,2-a]benzimidazole-2-carboxamidehydrochloride); (YM-193167 (6-amino-N-cyclohexyl-N,3-dimethylthiazolo[3,2-a]benzimidazole-2-carboxamide); (NPS 2390 (Quinoxaline-2-carboxylic acid adamantan-1-ylamide); 3-(5-(pyridin-2-yl)-2H-tetrazol-2-yl)benzonitrile; 3-[3-fluoro-5-(5-pyridin-2-yl-2H-tetrazol-2-yl)phenyl]-4-methylpyridine; 3-fluoro-5-(5- pyridin-2-yl-2H-tetrazol-2-yl)benzonitrile; N-cyclohexyl-6-{[(2-methoxyethyl)(methyl)amino]methyl}-N-methylthiazolo[3,2-a]benzimidazole-2-carboxamide (YM-202074); Desmethyl-YM298198 (6-Amino-N-cyclohexyl-3-methylthiazolo[3,2-a]benzimidazole-2-carboxamide hydrochloride); MPEP hydrochloride (2-Methyl-6-(phenylethynyl)pyridine hydrochloride); (S)-MCPG ((S)-a-Methyl-4-carboxyphenylglycine); (RS)-MCPG ((RS)-a-Methyl-4-carboxyphenylglycine); E4CPG ((RS)-a-Ethyl-4-carboxyphenylglycine); Hexylhomoibotenic acid (a-Amino-4-hexyl-2,3-dihydro-3-oxo-5-isoxazolepropanoic acid; HexylHIBO); (S)-Hexylhomoibotenic acid ((S)-a-Amino-4-hexyl-2,3-dihydro-3-oxo-5-isoxazolepropanoic acid; (S)-HexylHIBO); EMQMCM (3-ethyl-2-methyl-quinolin-6-yl)-(4-methoxy-cyclohexyl)-methanone methanesulfonate); JNJ 16259685; R214127 (1-(3,4-dihydro-2H-pyrano[2,3-b]quinolin-7-yl)-2-phenyl-1-ethanone); (S)-3-Carboxy-4-hydroxyphenylglycine ((S)-3C4HPG); Anti-mGlu5 blocking peptide ([K]-SSPKYDTLIIRDYTQSSSSL); DFB (3,3'-Difluorobenzaldazine); DMeOB ([(3-Methoxyphenyl)methylene]hydrazone-3-methoxybenzalde hyde); Anti-mGlu5 (([K]-SSPKYDTLIIRDYTQSSSSL); or combinations thereof.

In some embodiments, the modulator of a Group I mGluR is S-(4-Fluoro-phenyl)-{3-[3-(4-fluoro-phenyl)-[1,2,4]oxadiazol-5-yl]-piperidin-1-yl}-methanone (ADX47273); 4-[1-(2-fluoropyridin-3-yl)-5-methyl-1H-1,2,3-triazol-4-yl]-N-isopropyl-N-methyl-3,6-dihydropyridine-1(2H)-carboxamide (FTIDC); 6-(3-methoxy-4-(pyridin-2-yl)phenyl)imidazole[2,1-b]thiazole; 2-(2-methoxy-4-(4-(pyridin-2-yl)oxazol-2-yl)phenyl)acetonitrile; 2-(4-(benzo[d]oxazol-2-yl)-2-methoxyphenyl)acetonitrile; 2-(4-(2,3-dihydro-1H-inden-2-ylamino)4a,5,6,7,8,8a-hexahydroquinazolin-2ylthio)ethanol; or combinations thereof.

In certain instances, modulation of mGlu receptors of groups II and III reduces or inhibits post-synaptic potentials by preventing or decreasing the formation of cAMP. In certain instances, this causes a reduction in the release of neurotransmitters, especially glutamate. In some instances, Group II and III mGlu receptors are localized presynaptically and agonism of Group II or Group III mGlu receptors decreases excitotoxicity.

GRM7 is the gene which encodes the mGlu7 receptor, a group III receptor. In certain instances, the agonism of mGlu7 results in a decrease in synaptic concentrations of glutamate. This ameliorates glutamate excitotoxicity.

In some embodiments, the agent which modulates a group II mGlu receptor is a group II mGlu receptor agonist. In some embodiments, the group II mGlu receptor agonist is LY389795 ((−)-2-thia-4-aminobicyclo-hexane-4,6-dicarboxylate); LY379268 ((−)-2-oxa-4-aminobicyclo-hexane-4,6-dicarboxylate); LY354740 ((+)-2-aminobicyclo-hexane-2,6dicarboxylate); DCG-IV ((2S,2'R,3'R)-2-(2',3'-dicarboxycyclopropyl)glycine); 2R,4R-APDC (2R,4R-4-aminopyrrolidine-2,4-dicarboxylate), (S)-3C4HPG ((S)-3-carboxy-4-hydroxyphenylglycine); (S)-4C3HPG ((S)-4-carboxy-3-hydroxyphenylglycine); L-CCG-I ((2S,1'S,2'S)-2-(carboxycyclopropyl)glycine); and/or combinations thereof.

In some embodiments, the group III mGlu receptor is mGlu7. In some embodiments, the agent which modulates the group III mGlu receptor is a group III mGlu receptor agonist. In some embodiments, the group III mGlu receptor agonist is ACPT-I ((1S,3R,4S)-1-aminocyclopentane-1,3,4-tricarboxylic acid); L-AP4 (L-(+)-2-Amino-4-phosphonobutyric acid); (S)-3,4-DCPG ((S)-3,4-dicarboxyphenylglycine); (RS)-3,4-DCPG ((RS)-3,4-dicarboxyphenylglycine); (RS)-4-phosphonophenylglycine ((RS)PPG); AMN082 (,N'-bis(diphenylmethyl)-1,2-ethanediamine dihydrochloride); DCG-IV ((2S,2'R,3'R)-2-(2',3'-dicarboxycyclopropyl)glycine); and/or combinations thereof. In some embodiments, the agonist of mGlu7 is AMN082. In some embodiments, the mGlu receptor modulator is 3,5-Dimethylpyrrole-2,4-dicarboxylic acid 2-propyl ester 4-(1,2,2-trimethyl-propyl) ester (3,5-dimethyl PPP); 3,3'-difluorobenzaldazine (DFB), 3,3'-dimlethoxybenzaldazine (DMeOB), 3,3'-dichlorobenzaldazine (DCB) and other allosteric modulators of mGluR$_5$ disclosed in Mol. Pharmacol. 2003, 64, 731-740; (E)-6-methyl-2-(phenyldiazenyl)pyridin-3-ol (SIB 1757); (E)-2-methyl-6-styrylpyridine (SIB 1893); 2-methyl-6-(phenylethynyl)pyridine (MPEP), 2-methyl-4-((6-methylpyridin-2-yl)ethynyl)thiazole (MTEP); 7-(Hydroxyimino)cyclopropa[b]chromen-1α-carboxylate ethyl ester (CPCCOEt), N-cyclohexyl-3-methylbenzo[d]thiazolo[3,2-a]imidazole-2-carboxamide (YM-298198), tricyclo[3.3.3.1]nonanyl quinoxaline-2-carboxamide (NPS 2390); 6-methoxy-N-(4-methoxyphenyl)quinazolin-4-amine (LY 456239); mGluR1 antagonists disclosed in WO2004/058754 and WO2005/009987; 2-(4-(2,3-dihydro-1H-inden-2-ylamino)-5,6,7,8-tetrahydroquinazolin-2-ylthio)ethanol; 3-(5-(pyridin-2-yl)-2H-tetrazol-2-yl)benzonitrile, 2-(2-methoxy-4-(4-(pyridin-2-yl)oxazol-2-yl)phenyl)acetonitrile; 2-(4-(benzo[d]oxazol-2-yl)-2-methoxyphenyl)acetonitrile; 6-(3-methoxy-4-(pyridin-2-yl)phenyl)imidazo[2,1-b]thiazole; and/or combinations thereof.

In some embodiments, the modulator of mGluR is a positive allosteric modulator of mGluR. Examples of positive allosteric modulators of mGluR include and are not limited to S-(4-Fluoro-phenyl)-{3-[3-(4-fluoro-phenyl)-[1,2,4]oxadiazol-5-yl]-piperidin-1-yl}-methanone (ADX47273), ADX71149 (Addex Partner), compounds described in Knoflach et al. *PNAS* 2001, 98, 13402, positive allosteric modulators of mGluR described therein are incorporated herein by reference, or the like. In some embodiments, a modulator of mGluR is a negative allosteric modulator of mGluR. Negative allosteric modulators of mGluR include and are not limited to fenobam, compounds described in Kew, *Pharmacology & Therapeutics*, 104, 233-244; compounds described in Marino et al. *Current Opinion in Pharmacology*, 6, 98-102, negative allosteric modulators of mGluR described therein are incorporated herein by reference, or the like.

In the CNS, modulators of metabotropic glutamate receptors, particularly Group I mGluRs, have been shown to affect synaptic plasticity and thus potentially memory and other key CNS functions. Systemic dosing of brain-penetrant modulators of Group I mGluRs could potentially cause side effects limiting their utility for the treatment of inner ear diseases. In certain embodiments described herein, Group I mGluR modulators are dosed directly to the cochlea, for example by delivering an extended release formulation onto the round window membrane. In certain embodiments, the use of such formulations results in marginal systemic and CNS exposure.

The term "agonist" refers to an agent that binds to a specific receptor and triggers a response in the cell. An agonist mimics the action of an endogenous ligand that binds to the same receptor.

The term "antagonist" refers to an agent that diminishes, inhibits, or prevents the action of another molecule or the activity of a receptor site. Antagonists include, but are not limited to, competitive antagonists, non-competitive antagonists, uncompetitive antagonists, partial agonists and inverse agonists.

Competitive antagonists reversibly bind to receptors at the same binding site (active site) as the endogenous ligand or agonist, but without activating the receptor.

Non-competitive antagonists (also known as allosteric antagonists) bind to a distinctly separate binding site from the agonist, exerting their action to that receptor via the other binding site. Non-competitive antagonists do not compete with agonists for binding. The bound antagonists may result in a decreased affinity of an agonist for that receptor, or alternatively may prevent conformational changes in the receptor required for receptor activation after the agonist binds.

Uncompetitive antagonists differ from non-competitive antagonists in that they require receptor activation by an agonist before they can bind to a separate allosteric binding site.

Partial agonists are defined as drugs which, at a given receptor, might differ in the amplitude of the functional response that they elicit after maximal receptor occupancy. Although they are agonists, partial agonists can act as a competitive antagonist if co-administered with a full agonist, as it competes with the full agonist for receptor occupancy and producing a net decrease in the receptor activation observed with the full agonist alone.

An inverse agonist can have effects similar to an antagonist, but causes a distinct set of downstream biological responses. Constitutively active receptors which exhibit intrinsic or basal activity can have inverse agonists, which not only block the effects of binding agonists like a classical antagonist, but inhibit the basal activity of the receptor.

Pharmaceutical Compositions and Routes of Administration

Delivery of the compound to patients is optionally accomplished orally, intravenously, subcutaneously, intraperitoneally, intramuscularly, rectally or topically. In specific embodiments, delivery of the compound to patients is accomplished by topical administration to the inner ear, as therapeutically effective doses with systemic administration may induce undesired side-effects. In some embodiments, a therapeutically effective amount of a pharmaceutical composition comprising a Group I mGluR receptor modulator is able to reach the site of the mGluR receptor mediated aberrant activity in the afflicted individual.

Administration of the compound to the inner ear is optionally accomplished by various delivery techniques. These include the use of devices or drug carriers to transport and/or deliver the compound in a targeted fashion to the membranes of the round or oval window, where it diffuses into the inner ear or is actively infused. Examples are otowicks (see e.g., U.S. Pat. No. 6,120,484 to Silverstein), round window catheters (see e.g., U.S. Pat. Nos. 5,421,818; 5,474,529; 5,476,446; 6,045,528; all to Arenberg, or U.S. Pat. No. 6,377,849 and its division 2002/0082554 to Lenarz), or various types of gels, foams, fibrins or other drug carriers, which are placed in the round window niche or on the oval window, and loaded with the compound for sustained release (see e.g., WO 97/38698 by Manning; Silverstein et al. 1999 *Otolaryagology-Head and Neck Surgery* 120:649-655; Balough et al. 1998 *Otolaryngology-Head and Neck Surgery* 119:427-431). They further include the use of devices which are inserted into the cochlear duct or any other part of the cochlea (see e.g., U.S. Pat. No. 6,309,410 to Kuzma). The compound is optionally administered to the inner ear by transtympanic injection, where the middle ear or part of it is filled by a solution or other carriers of the compound (see e.g., Hoffer et al. 2003 *Otolaryagologic Clinics of North America* 36:353-358).

Administration to the inner ear is by diffusion across the round window membrane, which is relatively easily accessible from the middle ear space, allows the inner ear to remain intact, thus avoiding any potential problems from leaking intracochlear fluids.

The compounds are optionally provided in any of a variety of formulations compatible with delivery across a middle-inner ear membrane, provided that such formulation is stable (i.e., not subject to degradation to an unacceptable amount at body temperature). The compound is optionally provided in any form suitable for delivery and diffusion of agent across the middle-inner ear membrane structure, e.g., solid, semi-solid, gel, liquid, suspension, emulsion, osmotic dosage formulation, diffusion dosage formulation, erodible formulation, etc. In one embodiment, the formulation is suitable for delivery using an implantable pump in connection with a catheter inserted near the round window niche of the inner ear, e.g., an osmotic pump.

Pharmaceutical grade organic or inorganic carriers, excipients and/or diluents are optionally included in the formulations. The formulations optionally comprise a buffer such as sodium phosphate at physiological pH value, physiological saline or both (i.e., phosphate buffered saline). Suitable excipients include dextrose, glycerol, alcohol (e.g., ethanol), and the like, and combinations of one or more thereof with vegetable oils, propylene glycol, polyethylene glycol, benzyl alcohol, benzyl benzoate, dimethyl sulfoxide (DMSO), organics, and the like to provide a suitable composition. In addition, if desired, the composition optionally comprises hydrophobic or aqueous surfactants, dispersing agents, wetting or emulsifying agents, isotonic agents, pH buffering agents, dissolution promoting agents, stabilizers, antiseptic agents and other typical auxiliary additives employed in the formulation of pharmaceutical preparations. In certain embodiments, the compound is provided in the formulation as a solution, a suspension, and/or as a precipitate.

In certain embodiments, a compound contained within the disclosed pharmaceutical composition is provided in the form of a pharmaceutically acceptable salt. Examples of such a salt include, but are not limited to, those formed with organic acids (e.g., acetic, lactic, citric, malic, formaric, tartaric, stearic, ascorbic, succinic, benzoic, methanesulfonic, toluenesulfonic, or pamoic acid), inorganic acids (e.g., hydrochloridic, nitric, diphosphoric, sulphuric, or phosphoric acid), and polymeric acids (e.g., tannic acid, carboxymethyl cel-lulose, polylactic, polyglycolic, or co-polymers of poly-lactic-glycolic acids).

Pharmaceutical compositions for any route of administration contain a therapeutically effective amount of a modulator specific to Group I mGluR (such as mGluR1 and/or mGluR5), and, as necessary, inorganic or organic, solid or liquid pharmaceutically acceptable carriers. Pharmaceutical compositions suited for topical administration to the inner ear include aqueous solutions or suspensions, which, e.g., in the case of lyophilized formulations that contain the modulator specific to Group I mGluR (such as mGluR1 and/or mGluR5) alone or together with a carrier, are prepared prior to use. They further include gels, which are biodegradable or non-biodegradable, aqueous or non-aqueous, or microsphere based. Examples of such a gel include, but are not limited to, poloxamers, hyaluronates, xyloglucans, chitosans, polyesters, poly(lactides), poly(glycolide) or their co-polymers PLGA, sucrose acetate isobutyrate, and glycerol monooleate. Pharmaceutical compositions suited for enteral or parenteral administration include tablets or gelatine capsules or aqueous solutions or suspensions as described above.

The pharmaceutical compositions are optionally sterilized and/or contain adjuvants, e.g., preservatives, stabilizers, wetting agents and/or emulsifiers, salts for regulating the osmotic pressure and/or buffers. In some embodiments, the pharmaceutical compositions described herein contain further pharmacologically active substances. They are prepared by any of the methods well known in the art of pharmacy, e.g., by conventional mixing, granulating, confectioning, dissolving or lyophilizing methods, and contain from about 0.01 to 100%, or from about 0.1 to 50% (lyophilisates up to 100%), of active ingredient.

In certain embodiment, the pharmaceutical composition is formulated for topical application. Suitable vehicles for otic administration are organic or inorganic substances, which are pharmaceutically acceptable and which do not react with the modulator specific to Group I mGluR (such as mGluR1 and/or mGluR5), for example saline, alcohols, vegetable oils, benzyl alcohols, alkylene glycols, polyethylene glycols, glycerol triacetate, gelatin, carbohydrates such as lactose or starch, magnesium, stearate, talc and petrolatum. The indicated preparations are sterilized and/or contain ancillary substances such as lubricants, preservatives, such as thimersal (e.g., at 50%), stabilizers and/or wetting agents, emulsifiers, salts to influence the osmotic pressure, buffer substances, colorants, and/or aromatizing substances.

Optionally, the pharmaceutical compositions also contain one or more other active ingredients, including other biologically active agents, such as antibiotics, e.g., fluoroquinolones, anti-inflammatory agents, e.g., steroids, cortisone, analgesics, antipyrine, benzocaine, procaine, etc. In one embodiment, the pharmaceutical composition contain a combination of a modulator of Group I mGluR and an iGluR modulator, such as the NMDA receptor antagonists disclosed in US 2007/0015272, including but not limited to D-2-amino-5-phosphonopentanoate (D-AP5), Dizocilpine (MK 801), 7-chlorokynurenate (7-CK) and Gacyclidine (GK-11).

Compositions for topical administration optionally comprise other ingredients which are pharmaceutically acceptable. For example, a topical excipient is selected that does not enhance delivery of the agent to the systemic circulation or to the central nervous system when administered to the ear. For example, the topical excipient do not have substantial occlusive properties, which enhance percutaneous transmission through the mucosa into the systemic circulation. Such occlusive vehicles include hydrocarbon bases, anhydrous absorption bases such as hydrophilic petrolatum and anhydrous lanolin (e.g., Aquaphor), and water-in-oil emulsion bases such as lanolin and cold cream. Instead, vehicles which are substantially non-occlusive are used, and generally include those which are water soluble, such as oil-in-water emulsion bases (creams or hydrophilic ointments) and water soluble bases such as polyethylene glycol-based vehicles and aqueous solutions gelled with various agents such as methylcellulose, hydroxyethyl cellulose, and hydroxypropyl methylcellulose (e.g., KY Gel).

Suitable topical excipients and vehicles are found in sources, such as Remington's Pharmaceutical Sciences, Vol. 18, Mack Publishing Co., Easton, Pa. (1990), in particular Chapter 87. For instance, biologically active agents are combined with enhancing agents which enhance the penetration of an agent.

The pharmaceutical compositions are optionally administered prior to development of the inner ear conditions characterized by excessive glutamate release and/or excitotoxicity, or after the inner ear conditions characterized by excessive glutamate release and/or excitotoxicity has been diagnosed. In certain embodiments, the amount to be administered varies, depending upon the method of administration, duration of therapy, the condition of the subject to be treated, the severity of the inner ear conditions characterized by excessive glutamate release and/or excitotoxicity, and the efficacy of the particular compound used, age, body weight, general state of health, sex, diet, time and route of administration, rate of excretion and drug combination ultimately will be decided by the attending physician.

A therapeutically effective dose is defined as an amount effective to suppress or reduce the inner ear conditions characterized by excessive glutamate release and/or excitotoxicity in the afflicted individual. As stated above, a therapeutically effective dose may vary, depending on the choice of specific mGluR receptor modulator for treatment and on the method of its administration. For example, a higher dose of an intravenously administered mGluR1 or mGluR5 receptor modulator would be required than that of the same pharmaceutical composition administered locally to the round window membrane or oval window of the ear. Additionally, a lower dose of an mGluR1 or mGluR5 receptor modulator would be required wherein the mGluR1 or mGluR5 receptor modulator binds the mGluR1 or mGluR5 receptor with a higher binding affinity than an m mGluR1 or mGluR5 receptor modulator that binds with a lower affinity. As a result, in this illustrative example, mGluR1 or mGluR5 receptor modulators with higher binding affinities for the mGluR1 or mGluR5 receptor are preferred.

The duration of therapy may also vary, depending on the specific form of the inner ear condition characterized by excessive glutamate release and/or excitotoxicity, for example, for which treatment is desired—acute, subacute, or chronic. In some embodiments, as a guide, shorter durations of therapy are sufficient when the inner ear condition characterized by excessive glutamate release and/or excitotoxicity does not recur once therapy has ceased. In some other embodiments, longer durations of therapy are employed for an individual in which the inner ear condition characterized by excessive glutamate release and/or excitotoxicity persists following short therapy.

Example Pharmaceutical Formulations: Controlled Release Formulations

Disclosed herein are controlled release formulations including at least one therapeutic agent for delivery to an inner ear target. Controlled release formulations described herein deliver the proper amount of drug to the site of action at the right time to obtain a therapeutic benefit. In general, controlled release drug formulations impart control over the release of drug with respect to site of release and time of release within the body. As discussed herein, controlled release refers to immediate release, delayed release, extended release and pulsatile release. Many advantages are offered by controlled release. First, controlled release of a pharmaceutical agent allows less frequent dosing and thus minimizes repeated treatment. Second, controlled release treatment results in more efficient drug utilization and less of the compound remains as a residue. Third, controlled release offers the possibility of localized drug delivery by placement of a delivery device or formulation at the site of disease. Still further, controlled release offers the opportunity to administer and release two or more different drugs, each having a unique release profile, or to release the same drug at different rates or for different durations, by means of a single dosage unit.

Controlled Release: Sustained Release

Sustained-release options include gel formulations, and include components such as mucoadhesives, penetration enhancers, bioadhesives, antioxidants, surfactants, buffering agents, diluents, salts and preservatives. To the extent viscosity considerations potentially limit the use of a syringe/needle delivery system, thermoreversible gels or post-administration viscosity-enhancing options are also envisioned, as well as alternative delivery systems, including pumps, microinjection devices and the like.

Gel Formulations

Gels, sometimes referred to as jellies, have been defined in various ways. For example, the United States Pharmacopoeia defines gels as semisolid systems consisting of either suspensions made up of small inorganic particles or large organic molecules interpenetrated by a liquid. Gels can further consist of a single-phase or a two-phase system. A single-phase gel consists of organic macromolecules distributed uniformly throughout a liquid in such a manner that no apparent boundaries exist between the dispersed macromolecules and the liquid. Single-phase gels are usually prepared from synthetic macromolecules (e.g., carbomer) or from natural gums, (e.g., tragacanth). In some embodiments, single-phase gels are generally aqueous, but will also be made using alcohols and oils. Two-phase gels consist of a network of small discrete particles.

Gels can also be classified as being hydrophobic or hydrophilic. The bases of a hydrophobic gel usually consists of a liquid paraffin with polyethylene or fatty oils gelled with colloidal silica, or aluminum or zinc soaps. In contrast, the bases of hydrophobic gels usually consists of water, glycerol, or propylene glycol gelled with a suitable gelling agent (e.g., tragacanth, starch, cellulose derivatives, carboxyvinylpolymers, and magnesium-aluminum silicates).

In certain embodiments, the rheology of the gel formulation is pseudo plastic, plastic, thixotropic, or dilatant.

Presented herein are gel formulations which do not require use of a thickening agent. Such gel formulations incorporate at least one pharmaceutically acceptable buffer. In one aspect is a gel formulation comprising a modulator specific to Group I mGluR (such as mGluR1 and/or mGluR5) and a pharmaceutically acceptable buffer. In another embodiment, the pharmaceutically acceptable excipient or carrier is a gelling agent.

In some embodiments, useful formulations also include one or more pH adjusting agents or buffering agents. Suitable pH adjusting agents or buffers include, but are not limited to acetate, bicarbonate, ammonium chloride, citrate, phosphate, pharmaceutically acceptable salts thereof and combinations or mixtures thereof. Such pH adjusting agents and buffers are included in an amount required to maintain pH of the composition between a pH of about 3 to about 9, and in one embodiment between a pH of about 6 and about 7, and in yet another embodiment at a pH of about 6.5. In a further embodiment the pH is between 6 and 8, in an additional embodiment is between 7 and 8, and in still another embodiment the pH is about 7.3.

In some embodiments, the pharmaceutical formulations described herein are stable with respect to pH over a period of any of at least about 1 day, at least about 2 days, at least about 3 days, at least about 4 days, at least about 5 days, at least about 6 days, at least about 1 week, at least about 2 weeks, at least about 3 weeks, at least about 4 weeks, at least about 5 weeks, at least about 6 weeks, at least about 7 weeks, at least about 8 weeks, at least about 1 month, at least about 2 months, at least about 3 months, at least about 4 months, at least about 5 months, or at least about 6 months. In other embodiments, the formulations described herein are stable with respect to pH over a period of at least about 1 week. Also described herein are formulations that are stable with respect to pH over a period of at least about 1 month.

Described herein are formulations comprising a modulator specific to Group I mGluR (such as mGluR1 and/or mGluR5) and a thickening agent. Suitable thickening agents include by way of example only, gelling agents and suspending agents. In one embodiment, the thickened formulation does not include a pharmaceutically acceptable buffer. In another embodiment, the thickened formulation includes a pharmaceutically acceptable buffer.

In one embodiment, the pharmaceutically acceptable thickened formulation comprises at least one gelling agent. In one embodiment, the pharmaceutical formulation is a thickened formulation comprising at least one modulator specific to Group I mGluR (such as mGluR1 and/or mGluR5) wherein the compound is utilized at a concentration of about 0.005 mg to about 5 mg per gram of gelling agent. In another embodiment is a modulator specific to Group I mGluR (such as mGluR1 and/or mGluR5) utilized at a concentration of about 1 mg to about 5 mg per gram of gelling agent. In another embodiment is a modulator specific to Group I mGluR (such as mGluR1 and/or mGluR5) utilized at a concentration of about 0.005 mg to about 0.05 mg per gram of gelling agent. In another embodiment is a modulator specific to Group I mGluR (such as mGluR1 and/or mGluR5) utilized at a concentration of about 0.05 mg to about 0.5 mg per gram of gelling agent. In another embodiment is a modulator specific to Group I mGluR (such as mGluR1 and/or mGluR5) utilized at a concentration of about 0.5 mg to about 5 mg per gram of gelling agent. In another embodiment is a modulator specific to Group I mGluR (such as mGluR1 and/or mGluR5) utilized at a concentration of about 0.1 mg to about 5 mg per gram of gelling agent.

Suitable gelling agents for use in preparation of the gel formulation include, but are not limited to, celluloses, cellulose derivatives, cellulose ethers (e.g., carboxymethylcellulose, ethylcellulose, hydroxyethylcellulose, hydroxymethylcellulose, hydroxypropylmethylcellulose, hydroxypropylcellulose, methylcellulose), guar gum, xanthan gum, locust bean gum, alginates (e.g., alginic acid), silicates, starch, tragacanth, carboxyvinyl polymers, carrageenan, paraffin, petrolatum and any combinations or mixtures thereof. In some other embodiments, hydroxypropylmethylcellulose (Methocel®) is utilized as the gelling agent. In certain embodiments, the thickening agents described herein are also utilized as the gelling agent for the gel formulations presented herein.

In one embodiment is a modulator specific to Group I mGluR (such as mGluR1 and/or mGluR5) in a pharmaceutically acceptable thickened formulation wherein the formulation comprises at least one suspending agent.

Suspending agents include by example only, compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol can have a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like. In some embodiments, useful aqueous suspensions also contain one or more polymers as suspending agents. Useful polymers include water-soluble polymers such as cellulosic polymers, e.g., hydroxypropyl methylcellulose, and water-insoluble polymers such as cross-linked carboxyl-containing polymers.

In some embodiments, the formulations include excipients, other medicinal or pharmaceutical agents, carriers, adjuvants, such as preserving, stabilizing, wetting or emulsifying agents, solution promoters, and salts. In some embodiments, the excipients, carriers, adjuvants, are useful in forming a pharmaceutically acceptable thickened formulation. In some embodiments, the thickened formulation comprises a stabilizer. In another embodiment the formulation comprises a solubilizer. In a further embodiment the formulation comprises an antifoaming agent. In yet a further embodiment, the formulation comprises an antioxidant. In yet another embodiment, the formulation comprises a dispersing agent. In one embodiment, the formulation comprises a surfactant. In yet another embodiment, the formulation comprises a wetting agent.

In a specific embodiment, the formulation alternatively comprises a cyclodextrin. Cyclodextrins are cyclic oligosaccharides containing 6, 7, or 8 glucopyranose units, referred to as α-cyclodextrin, β-cyclodextrin, or γ-cyclodextrin respectively. Cyclodextrins have been found to be particularly useful in pharmaceutical formulations. Example cyclodextrins are the β-cyclodextrins, including hydroxypropyl-β-cyclodextrin (HPβCD).

In some embodiments, the pharmaceutical formulations described herein are stable with respect to compound degradation over a period of any of at least about 1 day, at least about 2 days, at least about 3 days, at least about 4 days, at least about 5 days, at least about 6 days, at least about 1 week, at least about 2 weeks, at least about 3 weeks, at least about 4 weeks, at least about 5 weeks, at least about 6 weeks, at least about 7 weeks, at least about 8 weeks, at least about 1 month, at least about 2 months, at least about 3 months, at least about 4 months, at least about 5 months, or at least about 6 months. In other embodiments, the formulations described herein are stable with respect to compound degradation over a period of at least about 1 week. Also described herein are formulations that are stable with respect to compound degradation over a period of at least about 1 month.

Presented below are examples of potential controlled release excipients:

| Example Formulation | Example Characteristics |
|---|---|
| Chitosan glycerophosphate (CGP) | tunable degradation of matrix in vitro<br>tunable VP2 modulator release in vitro: e.g., ~50% of drug released after 24 hrs<br>biodegradable<br>compatible with drug delivery to the inner ear<br>suitable for macromolecules and hydrophobic drugs |
| PEG-PLGA-PEG triblock polymers | tunable high stability: e.g., maintains mechanical integrity >1 month in vitro<br>tunable fast release of hydrophilic drugs: e.g., ~50% of drug released after 24 hrs, and remainder released over ~5 days<br>tunable slow release of hydrophobic drugs: e.g., ~80% released after 8 weeks<br>biodegradable<br>subcutaneous injection of solution: e.g., gel forms within seconds and is intact after 1 month |
| PEO-PPO-PEO triblock copolymers (e.g., Pluronic or Poloxameres) (e.g., F127) | Tunable sol-gel transition temperature: e.g., decreases with increasing F127 concentration |
| Chitosan glycerophosphate with drug-loaded liposomes | CGP formulation tolerates liposomes: e.g., up to 15 uM/ml liposomes.<br>liposomes tunably reduce drug release time (e.g., up to 2 weeks in vitro).<br>increase in liposome diameter optionally reduces drug release kinetics (e.g., liposome size between 100 and 300 nm)<br>release parameters are controlled by changing composition of liposomes |

The formulations disclosed herein alternatively encompass an otoprotectant agent in addition to the at least one modulator specific to Group I mGluR (such as mGluR1 and/or mGluR5) and/or excipients, including but not limited to such as antioxidants, alpha lipoic acid, calcium, fosfomycin or iron chelators, to counteract potential ototoxic effects that may arise from the use of specific therapeutic agents or excipients, diluents or carriers.

Penetration Enhancers

In another embodiment the formulation further comprises one or more penetration enhancers. Penetration into biological membranes can be enhanced by the presence of penetration enhancers. Penetration enhancers are chemical entities that facilitate transport of coadministered substances across biological membranes. Penetration enhancers can be grouped according to chemical structure. Surfactants, both ionic and non-ionic, such as sodium lauryl sulfate, sodium laurate, polyoxyethylene-20-cetyl ether, laureth-9, sodium dodecylsulfate, dioctyl sodium sulfosuccinate, polyoxyethylene-9-lauryl ether (PLE), Tween 80, nonylphenoxypolyethylene (NP-POE), polysorbates and the like, function as penetration enhancers. Bile salts (such as sodium glycocholate, sodium deoxycholate, sodium taurocholate, sodium taurodihydrofusidate, sodium glycodihydrofusidate and the like), fatty acids and derivatives (such as oleic acid, caprylic acid, mono- and di-glycerides, lauric acids, acylcholines, caprylic acids, acylcarnitines, sodium caprates and the like), chelating agents (such as EDTA, citric acid, salicylates and the like), sulfoxides (such as dimethyl sulfoxide (DMSO), decylmethyl sulfoxide and the like), and alcohols (such as ethanol, isopropanol, propylene glycol, polyethylene glycol, glycerol, propanediol and the like) also function as penetration enhancers.

Controlled Release: Kinetics

In one embodiment, the formulations disclosed herein additionally provides an immediate release of a modulator specific to Group I mGluR (such as mGluR1 and/or mGluR5). In certain embodiments, diffusion of at least one modulator specific to Group I mGluR (such as mGluR1 and/or mGluR5) from the formulation occurs immediately, or within 1 minute, or within 5 minutes, or within 10 minutes, or within 15 minutes, or within 30 minutes, or within 60 minutes or within 90 minutes. In other embodiments, a therapeutically effective amount of at least one modulator specific to Group I mGluR (such as mGluR1 and/or mGluR5) is released from the formulation immediately, or within 1 minute, or within 5 minutes, or within 10 minutes, or within 15 minutes, or within 30 minutes, or within 60 minutes or within 90 minutes. In certain embodiments the formulation comprises a gel formulation providing immediate release of at least one modulator specific to Group I mGluR (such as mGluR1 and/or mGluR5).

In one embodiment, the formulation provides an extended release formulation of at least one modulator specific to Group I mGluR (such as mGluR1 and/or mGluR5). In certain embodiments, diffusion of at least one modulator specific to Group I mGluR (such as mGluR1 and/or mGluR5) from the formulation occurs for a time period exceeding 15 minutes, or 30 minutes, or 1 hour, or 4 hours, or 6 hours, or 12 hours, or 18 hours, or 1 day, or 2 days, or 3 days, or 4 days, or 5 days, or 6 days, or 7 days, or 10 days, or 12 days, or 14 days, or 18 days, or 21 days, or 25 days, or 30 days, or 45 days, or 2 months or 3 months or 4 months or 5 months or 6 months or 9 months or 1 year. In other embodiments, a therapeutically effective amount of at least one modulator specific to Group I mGluR (such as mGluR1 and/or mGluR5) is released from the formulation for a time period exceeding 15 minutes, or 30 minutes, or 1 hour, or 4 hours, or 6 hours, or 12 hours, or 18 hours, or 1 day, or 2 days, or 3 days, or 4 days, or 5 days, or 6 days, or 7 days, or 10 days, or 12 days, or 14 days, or 18 days, or 21 days, or 25 days, or 30 days, or 45 days, or 2 months or 3 months or 4 months or 5 months or 6 months or 9 months or 1 year.

In other embodiments, the formulation provides both an immediate release and an extended release formulation of an modulator specific to Group I mGluR (such as mGluR1 and/or mGluR5). In yet other embodiments, the formulation contains a 0.25:1 ratio, or a 0.5:1 ratio, or a 1:1 ratio, or a 1:2 ratio, or a 1:3, or a 1:4 ratio, or a 1:5 ratio, or a 1:7 ratio, or a 1:10 ratio, or a 1:15 ratio, or a 1:20 ratio of immediate release and extended release formulations. In a further embodiment the formulation provides an immediate release of a first modulator specific to Group I mGluR (such as mGluR1 and/or mGluR5) and an extended release of a second active pharmaceutical ingredient. In yet other embodiments, the formulation provides an immediate release and extended release formulation of at least two active pharmaceutical ingredients. In some embodiments, the formulation provides a 0.25:1 ratio, or a 0.5:1 ratio, or a 1:1 ratio, or a 1:2 ratio, or a 1:3, or a 1:4 ratio, or a 1:5 ratio, or a 1:7 ratio, or a 1:10 ratio, or a 1:15 ratio, or a 1:20 ratio of immediate release and extended release formulations of a first and second active pharmaceutical agent, respectively.

In a specific embodiment the formulation provides a therapeutically effective amount of at least one modulator specific to Group I mGluR (such as mGluR1 and/or mGluR5) at the site of disease with no systemic exposure. In an additional embodiment the formulation provides a therapeutically effective amount of at least one modulator specific to Group I mGluR (such as mGluR1 and/or mGluR5) at the site of disease with no detectable systemic exposure.

Dosing Options

Intratympanic injection of therapeutic agents is the technique of injecting a therapeutic agent behind the tympanic membrane into the middle and/or inner ear. Despite early success with this technique (Schuknecht, Laryngoscope (1956) 66, 859-870) some challenges do remain. Access to the round window membrane, the site of drug absorption into the inner ear, can be challenging. In one embodiment, the formulation described herein is administered directly onto the round window membrane via transtympanic injection. In another embodiment, the formulation described herein is administered onto the round window membrane via a non-transtympanic approach to the inner ear. In additional embodiments, the formulation described herein is administered onto the round window membrane via a surgical approach to the round window membrane comprising modification of the crista fenestrae.

The compositions containing the compound(s) described herein are administered for prophylactic and/or therapeutic treatments. In therapeutic applications, the compositions are administered to a patient already suffering from a disease, condition or disorder, in an amount sufficient to cure or at least partially arrest the symptoms of the disease, disorder or condition. Amounts effective for this use will depend on the severity and course of the disease, disorder or condition, previous therapy, the patient's health status and response to the drugs, and the judgment of the treating physician.

In the case wherein the patient's condition does not improve, upon the doctor's discretion the administration of the compounds are administered chronically, that is, for an extended period of time, including throughout the duration of the patient's life in order to ameliorate or otherwise control or limit the symptoms of the patient's disease or condition.

In the case wherein the patient's status does improve, upon the doctor's discretion the administration of the compounds is given continuously; alternatively, the dose of drug being administered is temporarily reduced or temporarily suspended for a certain length of time (i.e., a "drug holiday"). The length of the drug holiday can vary between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, and 365 days. The dose reduction during a drug holiday is from 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained. Patients can, however, require intermittent treatment on a long-term basis upon any recurrence of symptoms.

The amount of a given agent that will correspond to such an amount will vary depending upon factors such as the particular compound, disease condition and its severity, and is determined according to the particular circumstances surrounding the case, including, e.g., the specific agent being administered, the route of administration, the condition being treated, and the subject or host being treated. In some embodiments, doses employed for adult human treatment are in the range of 0.02-50 mg per administration, or 1-15 mg per administration. The desired dose is conveniently presented in a single dose or as divided doses administered simultaneously (or over a short period of time) or at appropriate intervals.

In some embodiments, the initial administration is of a particular formulation and the subsequent administration is of a different formulation or active pharmaceutical ingredient.

Kits and Other Articles of Manufacture

The disclosure also provides kits for preventing, treating or ameliorating the symptoms of a diseases or disorder in a mammal. Such kits generally will comprise one or more of the pharmaceutically acceptable gel-based compositions as disclosed herein, and instructions for using the kit. The disclosure also contemplates the use of one or more of the formulations, in the manufacture of medicaments for treating, abating, reducing, or ameliorating the symptoms of a disease, dysfunction, or disorder in a mammal, such as a human that has, is suspected of having, or at risk for developing an inner ear disorder.

In some embodiments, kits include a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. In other embodiments, the containers are formed from a variety of materials such as glass or plastic.

The articles of manufacture provided herein contain packaging materials. Packaging materials for use in packaging pharmaceutical products presented herein. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disease, disorder, or condition that would benefit by extended release administration of a therapeutic agent to the inner ear.

In some embodiments, a kit will typically includes one or more additional containers, each with one or more of various materials (such as reagents, optionally in concentrated form, and/or devices) desirable from a commercial and user standpoint for use of a formulation described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included.

In a further embodiment, a label is on or associated with the container. In yet a further embodiment, a label is on a container when letters, numbers or other characters forming the label are attached, molded or etched into the container itself; a label is associated with a container when it is present within a receptacle or carrier that also holds the container, e.g., as a package insert. In other embodiments a label is used to indicate that the contents are to be used for a specific therapeutic application. In yet another embodiment, a label also indicates directions for use of the contents, such as in the methods described herein.

In certain embodiments, the pharmaceutical compositions are presented in a pack or dispenser device which contains one or more unit dosage forms containing a compound provided herein. In another embodiment, the pack for example contains metal or plastic foil, such as a blister pack. In a further embodiment, the pack or dispenser device is accompanied by instructions for administration. In yet a further embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. In another embodiment, such notice, for example, is the labeling approved by the U.S. Food and Drug Administration for prescription drugs, or the approved product insert. In yet another embodiment, compositions containing a compound provided herein formulated in a compatible pharmaceutical carrier are also prepared, placed in an appropriate container, and labeled for treatment of an indicated condition.

EXAMPLES

Example 1

Preparation of a Gel 4-[1-(2-fluoropyridin-3-yl)-5-methyl-1H-1,2,3-triazol-4-yl]-N-isopropyl-N-methyl-3,6-dihydropyridine-1(2H)-carboxamide (FTIDC) Formulation

| Ingredient | Quantity (mg/g of formulation) |
| --- | --- |
| FTIDC | 16 |
| chitosan | 8 |
| Glycerophosphate disodium | 32 |
| water | 336 |

A 5 ml solution of acetic acid is titrated to a pH of about 4.0. The chitosan is added to achieve a pH of about 5.5. The FTIDC is then dissolved in the chitosan solution. This solution is sterilized by filtration. A 5 ml aqueous solution of glycerophosphate disodium is also prepared and sterilized. The two solutions are mixed and within 2 h at 37° C., the desired gel is formed.

Example 2

Application of a Gel 4-[1-(2-fluoropyridin-3-yl)-5-methyl-1H-1,2,3-triazol-4-yl]-N-isopropyl-N-methyl-3,6-dihydropyridine-1(2H)-carboxamide (FTIDC) Formulation onto the Round Window Membrane A formulation according to Example 1 is prepared and loaded into 5 ml siliconized glass syringes attached to a 26-27-gauge luer lock disposable needle. The gel 4-[1-(2-fluoropyridin-3-yl)-5-methyl-1H-1,2,3-triazol-4-yl]-N-isopropyl-N-methyl-3,6-dihydropyridine-1(2H)-carboxamide formulation is topically applied to the tympanic membrane, and a small incision made to allow visualization into the middle ear cavity. The needle tip is guided into place over the round window membrane, and the gel FTIDC formulation applied directly onto the round-window membrane.

Example 3

Evaluation of FTIDC in an Early Onset Age-Related Hearing Impairment DBA-Mouse Model DBA mice are administered an FTIDC formulation of Example 1 directly onto the round window membrane, beginning 2, 4 or 8 weeks after birth. The hearing threshold for the auditory brainstem response threshold (ABR) to click stimuli for each ear of each animal is initially measured and on a weekly basis during and after the experimental procedure. The animals are placed in a single-walled acoustic booth (Industrial Acoustics Co, Bronx, N.Y., USA) on a heating pad. Subdermal electrodes (Astro-Med, Inc. Grass Instrument Division, West Warwick, R.I., USA) were inserted at the vertex (active electrode), the mastoid (reference), and the hind leg (ground). Click stimuli (0.1 millisecond) are computer generated and delivered to a Beyer DT 48, 200 Ohm speaker fitted with an ear speculum for placement in the external auditory meatus. The recorded ABR is amplified and digitized by a battery-operated preamplifier and input to a Tucker-Davis Technologies ABR recording system that provides computer control of the stimulus, recording, and averaging functions (Tucker Davis Technology, Gainesville, Fla., USA). Successively decreasing amplitude stimuli are presented in 5-dB steps to the animal, and the recorded stimulus-locked activity is averaged (n=512) and displayed. Threshold is defined as the stimulus level between the record with no visibly detectable response and a clearly identifiable response.

Example 4

Clinical Trials of FTIDC in Tinnitus Patients

Study Objective

The primary objective of this study will be to assess the safety and efficacy of FTIDC compared with that of placebo in ameliorating tinnitus symptoms in afflicted patients.

Study Design

This will be a phase 3, multicenter, double-blind, randomized, placebo-controlled, two-arm study comparing FTIDC to placebo in the treatment of tinnitus. Approximately 250 subjects will be enrolled in this study, and randomized (1:1) to 1 of 2 treatment groups. Each group will receive 300 mg FTIDC delivered in a controlled-release gel, or a controlled release placebo formulation. Release of FTIDC is occurs over 14 days; the route of administration will be intratympanic injection.

Primary Outcome Measure

Visual Analog Scales (VAS) to measure the change in tinnitus loudness as perceived at the moment of the measurement at 2 hrs after dosing (or at any other time point vs. pre-dose baseline).

Inclusion Criteria

Patients may be included if they meet any of the following criteria:
Male or female subjects with a persistent, subjective, uni or bi-lateral tinnitus tinnitus.
Subjects willing to restrict alcohol intake.
Women of childbearing potential who abstain from intercourse OR agree to birth control.
Women of non-childbearing potential.

Exclusion Criteria

Patients may be excluded if they meet any of the following criteria:
Intermittent or pulsatile tinnitus
Subject with pathologic level of anxiety or depression.
Subject with no audiogram deficit and with normal hearing.
Subjects that do not respond to the lidocaine infusion test or show a large variability in pre-infusion values.
Existence of any surgical or medical condition which might interfere with the PK of the drug.
Subjects with hepatic impairment or a history of liver dysfunction.
Subjects with renal impairment.
Subjects positive for HIV, hepatitis C or hepatitis B.
Subjects with abnormal laboratory, ECG or physical examination findings.
Subjects who are not euthyroid.
Subjects with a history of hepatic, cardiac, renal, neurologic, cerebrovascular, metabolic or pulmonary disease.
Subjects who have had a myocardial infarction.
Subjects with a history of seizure disorders.
Subjects with history of cancer.
Subjects with a history of drug or other allergy.
Subjects positive for drug use and/or a history of substance abuse or dependence.
Subjects who have taken psychotropic drugs or antidepressants within specified time frames.
Medication or foodstuff (e.g. grapefruit or grapefruit juice) which is known to interfere with liver enzymes.
Subjects who have recently used an investigational drug or recently participated in a trial.
Women who have a positive pregnancy test.
Female subjects who intend to get pregnant or male subjects who intend to father a child within the next 4 weeks following the last study drug administration in the study.
Subjects, who have donated a unit of blood or more within the previous month or who intend to donate blood within one month of completing the study.

Example 5

Administration to Patients in Need

A 65 year old man presents with symptoms of presbycusis, including moderate loss of higher frequency (above 2000 Hz) hearing (50 decibel threshold) in both ears. The man is administered two drops per ear twice daily of a topical otic formulation comprising 10 ug/ml of FTIDC in a phosphate-buffered saline and further comprising 0.25% the carboxyvinyl water swellable gelling agent, Carbopol 934P; i.e., about 1 ug of FTIDC per ear per dosing. After 14 days, the patient is tested by an audiologist. The threshold is lowered to 35 decibels right ear and 40 decibels left ear.

A 72 year old woman presents with symptoms of presbycusis, including loss of moderately high frequency (above 1000 Hz) hearing (40 decibel threshold right ear and 35 decibel threshold left ear). The woman is administered an oral formulation 4 times per day comprising 2 ug per dose of FTIDC. The extended release capsule comprises a matrix of 10% by weight hydroxypropyl methylcellulose (e.g., Methocel®; Dow Chemical Company, U.S.A), and 50% by weight of a cornstarch filler. After 14 days, the threshold is lowered to 35 decibels right ear and 25 decibels left ear.

An 82 year old man presents with symptoms of presbycusis, including loss of hearing in the 500 to above 2000 Hz range. The man is implanted with an Alset® osmotic pump adapted for cochlear delivery; see e.g., Richardson, R. T., Noushi, F., O'Leary, S. Inner ear therapy for neural preservation. AUDIOLOGY AND NEURO-OTOLOGY 2006; 11(6): 343-356. The pump is supplied with an aqueous sterile solution comprising FTIDC. The pump delivers a dose of 10 ug/hour of the modulator. After 10 days, hearing is improved in both ears.

While preferred embodiments of the present invention have been shown and described herein, it will be obvious to those skilled in the art that such embodiments are provided by way of example only.

Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for treating inner ear conditions associated with or characterized by aberrant glutamatergic signaling in the inner ear, comprising administration of a pharmaceutical composition comprising an amount of a modulator of a Group I mGluR sufficient to treat the conditions, wherein the composition is a controlled release gel formulation administered on or near the round window membrane of the inner ear, wherein the modulator of a Group I mGluR is 4-[1-(2-fluoropyridin-3-yl)-5-methyl-1H-1,2,3-triazol-4-yl]-N-isopropyl-N-methyl-3,6-dihydropyridine-1(2H)-carboxamide (FTIDC), and wherein the inner ear condition is selected from excitotoxicity, presbycusis, tinnitus, and noise-induced hearing loss.

2. The method of claim 1, wherein the controlled release formulation is a sustained release formulation.

3. The method of claim 1, wherein the controlled release formulation is an immediate release formulation.

4. The method of claim 1, wherein the aberrant glutamatergic signaling is excessive activity and/or excitotoxicity.

5. The method of claim 1, wherein the aberrant glutamatergic signaling is insufficient activity.

* * * * *